(12) United States Patent
Foley

(10) Patent No.: US 6,535,223 B1
(45) Date of Patent: Mar. 18, 2003

(54) METHOD AND SYSTEM FOR DETERMINING PUPILTARY DISTANT AND ELEMENT HEIGHT

(75) Inventor: Christopher Foley, St. Cloud, MN (US)

(73) Assignee: Schmidt Laboratories, Inc., St. Cloud, MN (US)

( * ) Notice: Subject to any disclaimer, the term of this patent is extended or adjusted under 35 U.S.C. 154(b) by 0 days.

(21) Appl. No.: 09/584,061

(22) Filed: May 31, 2000

(51) Int. Cl.$^7$ ................................................ G09G 5/00
(52) U.S. Cl. ..................... 345/629; 345/632; 351/204
(58) Field of Search ................................. 345/629, 630, 345/632, 633, 634, 642, 646; 351/204, 205

(56) References Cited

U.S. PATENT DOCUMENTS

| | | |
|---|---|---|
| 4,539,585 A | 9/1985 | Spackova |
| 4,845,641 A | 7/1989 | Ninomiya |
| 4,852,184 A | 7/1989 | Tamura |
| 5,280,570 A | 1/1994 | Jordan |
| 5,592,248 A | 1/1997 | Norton |
| 5,617,155 A | 4/1997 | Ducarouge |
| 6,095,650 A | 8/2000 | Gao |

Primary Examiner—Matthew Luu
(74) Attorney, Agent, or Firm—Beck & Tysver, P.L.L.C.

(57) ABSTRACT

A method and system is presented for determining pupillary distance and multi-focal element height for prescription eyeglasses via images received through a computer network. The received image has a reference object of a known real-world size located approximately the same distance from the camera as the face. The size of the reference object on the image is determined, such as by measuring the number of pixels across the reference object. A scale for the image is determined by dividing the real world width of the reference object by the image size of the reference object. An image value for the pupillary distance and multi-focal element height is then determined. The scale value is applied to the image value to determine the real-world pupillary distance and multi-focal element height for the patient. The reference object can be a generally available object such as a monetary coin, or a facial element that has a relatively fixed size from face to face, such as the size of the iris. Image sizes can be determined by presenting the image to an individual, or through image recognition technology.

31 Claims, 7 Drawing Sheets

METHOD AND SYSTEM FOR DETERMINING PUPILTARY DISTANT AND ELEMENT HEIGHT

TECHNICAL FIELD

The present invention relates to a method and system for determining pupillary distance and multi-focal element height for prescription eyeglasses via images received through a computer network.

BACKGROUND OF THE INVENTION

In the United States, the market for ophthalmic goods such as glasses and contact lenses is estimated to exceed over sixteen billion dollars. As with other retail markets, the leaders in providing eyeglasses have recently begun to move retail sales to the Internet in order to expand their market share. Consumers have benefited from the move by having access to a wider selection of frames at a cheaper price than can usually be obtained at a bricks and mortar retail store.

Unfortunately, sales of prescription eyewear over the Internet are limited because users are unable to actually try on frames before purchasing. In an effort to overcome this limitation, some retail eyewear providers operating on the Internet have utilized methods to "virtually" try on different frames through their web sites. In order to accomplish this, users will submit an electronically formatted image of their face to the retailer. The image can be created by using a digital camera or camcorder, by scanning in a conventional photograph, or through any other known technique. The submitted facial image is then stored on the retailer's server and is associated with a particular client for all future transactions.

Once the facial image is stored on a server, software programs known in the art can combine the photograph with stored images (or some type of image definition) of eyeglass frames. The user is then invited to select a pair of frames to "try on." Once the pair is selected, the stored facial image is superimposed with an image of the selected frame. This combined image is then presented to the user so that the user sees their own image wearing the selected frame.

This "virtual try-on" technique should greatly assist Internet retails sales of prescription eyeglasses. However, the loss of the ability to try on glasses is only one of the disadvantages working against eyewear Internet sales. A second disadvantage is that most ophthalmic goods require a prescription indicating the vision correction required by the individual purchaser. As a result, web sites providing eyeglasses to customers must ask for specific prescription information.

One help to e-commerce in this area is that the Federal Trademark Commission (or FTC) has developed a "prescription release rule" that requires eye doctors (including both optometrist and ophthalmologists) to give their patients an eye glasses prescription immediately after an eye exam. By rule, this prescription must include the sphere, cylinder, and axis—the three components that determine the prescription needed to correct vision. The rule was enacted to ensure the patients would be free to shop for eyeglasses at locations other than their eye doctor's office. Prior to the rule, patients were often unable to obtain their prescriptions and as a result were only able to order lenses through their eye doctor, or were forced to see the eye doctor at their preferred retail location.

As a result of this rule, most individuals in the United States who require vision correction have easy access to their prescription. This has made it easier to purchase eyewear on the Internet, as the web site can simply request that users enter the information found on their prescription card. Unfortunately, one crucial element needed for grinding eye glass lenses usually is missing from the prescription provided by eye doctors under this rule, namely the pupillary distance (or, more accurately, "inter-pupillary distance"). This distance is the measurement from pupil to pupil, and is required to properly grind lenses for a particular set of frames.

Prior to Internet retail web sites, this was not a significant issue since any retailer could take the pupillary distances (or "PD") measurement upon examining the patient. With Internet sales of eye wear, it is impossible to obtain the PD measurement through direct measurement of the patient. At the present time, web sites must simply ask for the end user to provide the pupillary distance, just as the site asks for the vision correction prescription. Because the measurement is not found on the typical prescription card provided by the eye care professional, the web site must explain to the end user what is meant by pupillary distance. The site must then either advise users how to have this distance measured and recorded for them, or how to mark their own pupils on a mirror and measure the PD by measuring the distance between the marks.

Unfortunately, many customers are scared off by either having to measure the pupillary distance themselves or by contacting the bricks and mortar retailer that they hoped to avoid by shopping over the Internet. What is needed is a way to purchase prescription eyewear over the Internet that requires users to provide only the basic prescription information generally found on the optical prescription card provided under the FTC rules.

SUMMARY OF THE INVENTION

The present invention meets these needs by determining the pupillary distance for a user from an image provided for use with "virtual try-on" technology. This is accomplished by having the user place a reference object on or near their face in the virtual try-on image. The reference object should be one that is a standard size and is readily available to users. One example for the U.S. market is a U.S. quarter dollar. Alternatively, the reference object used can be the iris in a user's own eye, since it is well known that the human iris is of a relatively fixed size from individual to individual.

When using a reference object, the user takes the facial picture with the reference object on generally the same plane and distance from the camera as their face, such as by holding a quarter on their chin with a single finger. The image is then submitted to the web site as is now standard with sites utilizing virtual try-on technology.

After the image is transmitted, the image can then be resized and used to try-on different frames as is known in the prior art. Alternatively, a second image without a reference object can be used for trying on frames.

Once the frames are selected and an order for the frames placed, the image with the reference object is associated with the order. The width of the reference object on the image is then compared to the measured pupillary distance on the image. These measurements can be made in pixels as opposed to real-world distances, because the image is being provided in a pixelated digital file. The actual pupillary distance can then be calculated by comparing the ratio of the distances measured in the image with the known width of the reference object.

Similarly, the virtual pupillary distance or segment height (usually called "seg height") needed for multi-focal elements can be determined by measuring the height using the frame on face virtual try-on technology. The measured distance on the image is converted to a real world measurement using the ratio obtained from the reference image.

DETAILED DESCRIPTION OF THE INVENTION

Figure 1:
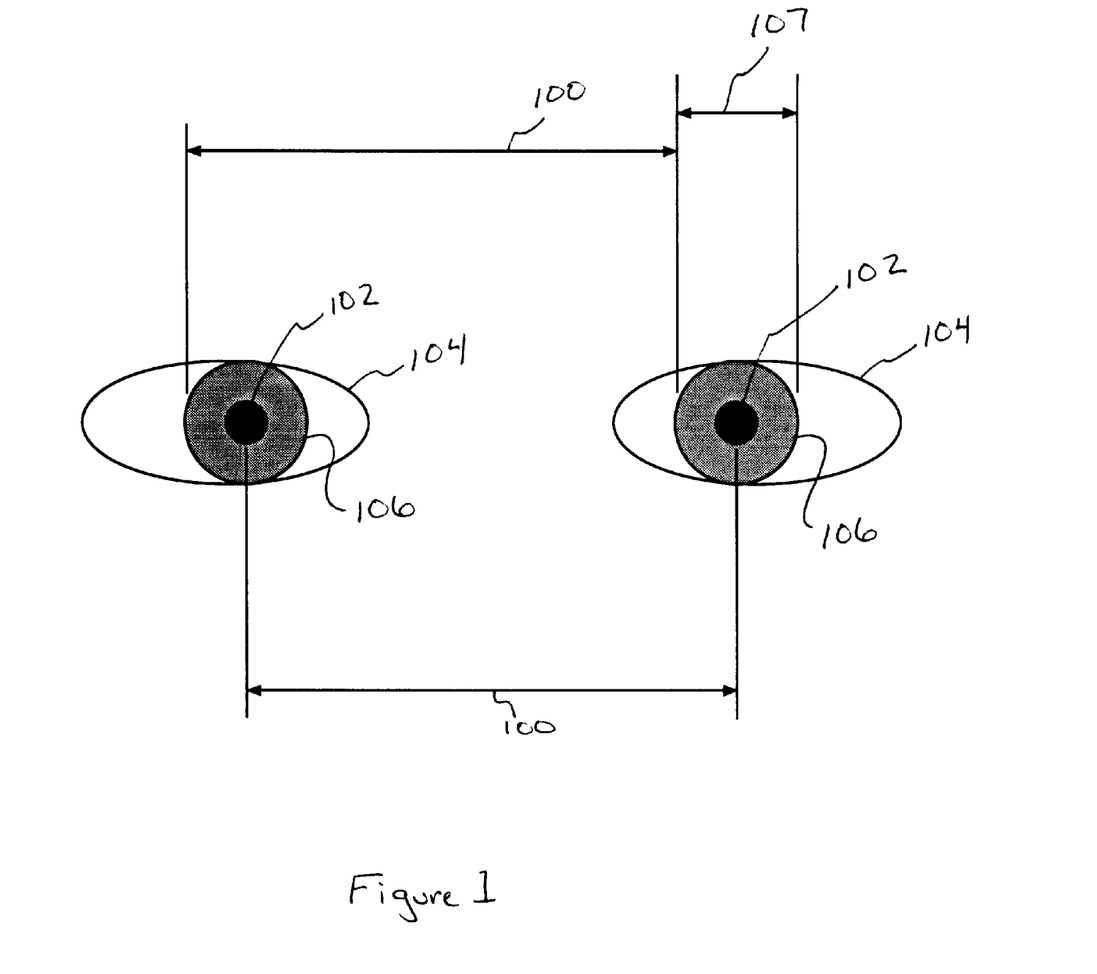
FIG. 1 is an illustration of a pair of eyes with significant distance parameters marked.

As shown in FIG. 1, the pupillary distance (or "PD") 100 is the measurement in millimeters from the center of the pupil 102 of one eye 104 to the center of the pupil 102 of the other eye 104. Due to the uniformity of the iris 106 and the consistency of location of the pupil 102 in the iris, it is also possible to take the PD measurement 100 by measuring the two irises 106. In this case, the measurement is made from the left (or right) edge of the iris 106 of one eye 104 to the same edge of the iris 106 of the other eye 104. This measurement is often easier to make than the direct pupil 102 to pupil 102 measurement, especially when the iris 106 is dark and there is little contrast between pupil 102 and iris 106. The contrast between the sclera (the white of the eye) and the iris 106 is much greater, making the measurement easier to take.

The PD measurement 100 is used to make sure that the lens prescription is ground on the correct point in the lens relative to the wearer's eyes 104. Specifically, the prism reference point of the lens in the frame must be aligned with pupils 102 of the wearer. If the PD measurement 100 is inaccurate, then the prism reference point will be positioned inaccurately for the user. This can result is inaccurate vision correction, visual discomfort, and sometimes even double vision. Consequently, it is impossible to correctly grind lenses for eyeglasses without the PD measurement 100.

To ensure an accurate PD measurement 100, various specialized devices have been created, including the pupilometer, the PD gauge, or the PD meter. In spite of these more sophisticated devices, many professionals still use a simple graduated ruler to take the measurement 100. The continued use of a simple ruler after the advent of more sophisticated instruments is primarily a result of the fact that a perfect PD measurement 100 is not necessary for accurate grinding. According to the American National Standards Index (ANSI) a PD measurement 100 that is accurate within two millimeters is sufficient for good lens production. In fact, with lower prescriptions an error of three millimeters is sometimes allowable.

Figure 2:
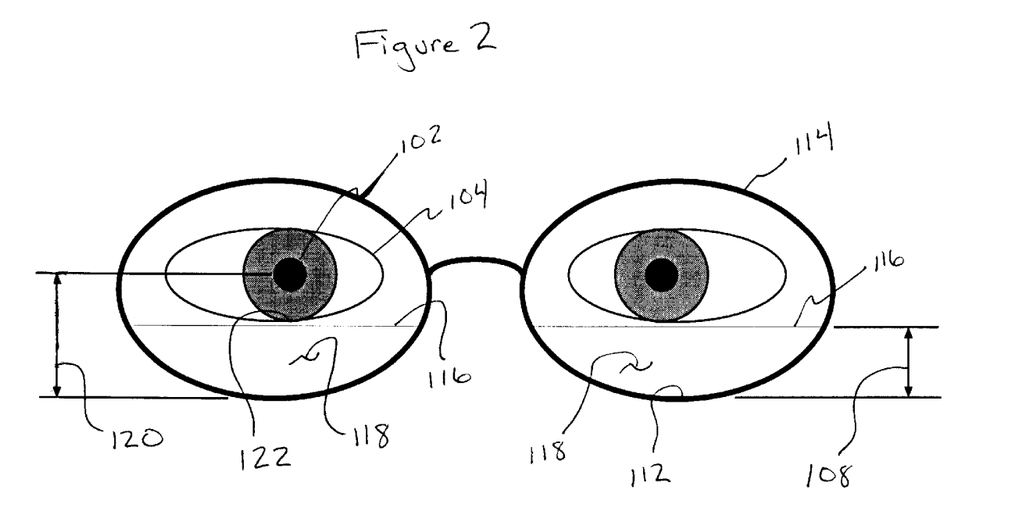
FIG. 2 is an illustration of a pair of eyes with glasses thereon.

In addition to the PD 100, another measurement is needed when manufacturing multi-focal lenses. In the present invention, all lenses with additional elements in them, such as bifocals, trifocals, and progressive addition lenses (no-line bifocals) are considered multi-focal lenses. The additionally needed measurement is known as the segment or "seg" height 108. As shown in FIG. 2, the seg height 108 is the distance from the extreme bottom 112 of the selected frame 114 to the top 116 of the multi-focal segment 118.

The seg height 108 is not generally prescribed by the eye care professional that determines the vision correction prescription. Rather, the retailer will make a determination where the seg height 108 should be located based upon the location of the eyes 104 in the frames 114. Generally, bifocal lens elements are placed so that the seg height 108 is at the lower lid 122 of the eye 104. A tri-focal seg height 108 would be at the bottom of the pupil. Progressive addition lenses have a seg height 108 that is approximately the same as the vertical pupillary distance (or "VPD") 120, which is the height of the center of the pupil 102 in the frame 114).

Figure 3:
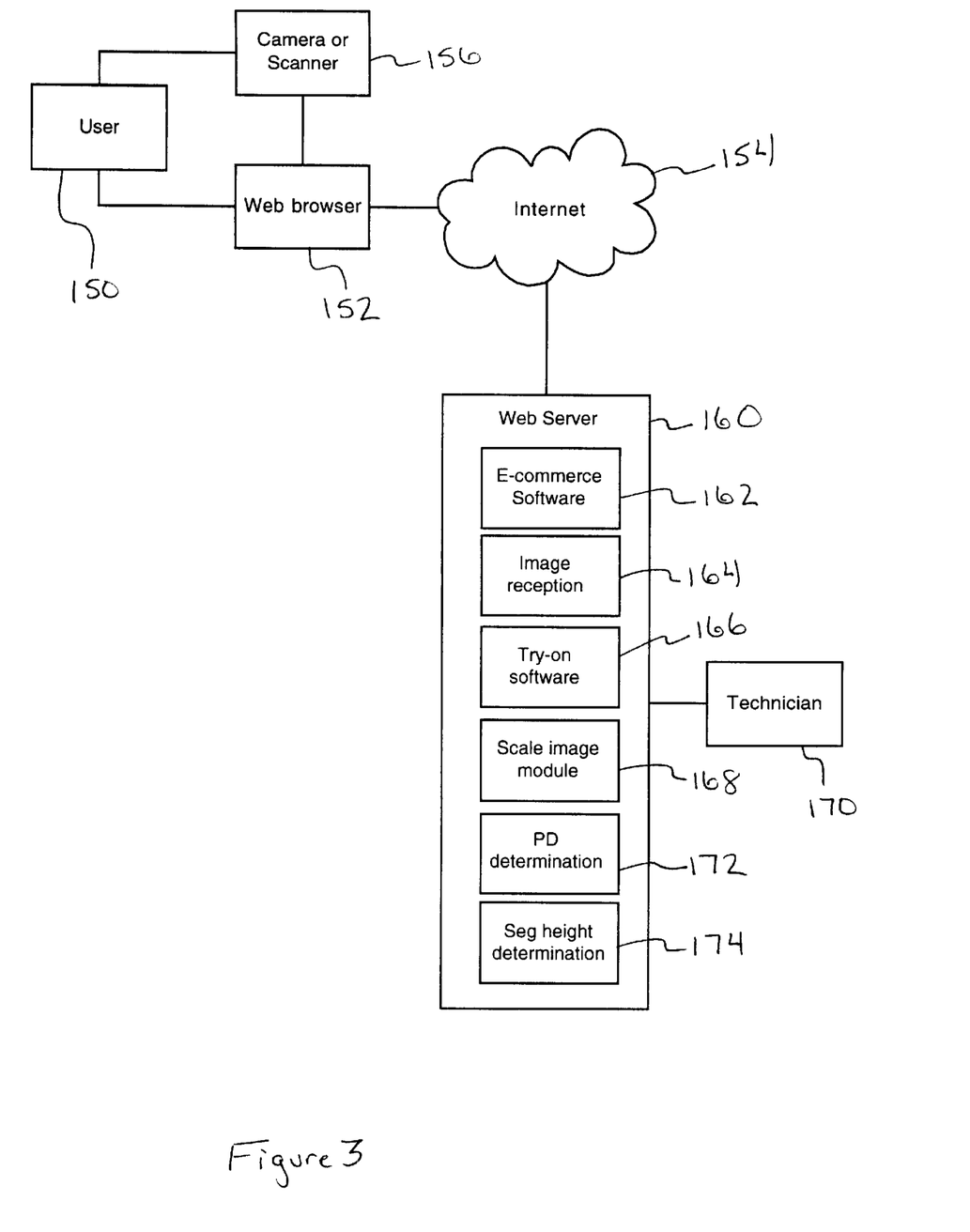
FIG. 3 is a schematic representation of a method and system for determining papillary distance and multi-focal element height for prescription eyeglasses via images received through a computer network.

The present invention allows an Internet seller of prescription eyewear to determine the PD 100 and the seg height 108 (or VPD 120) based upon an image submitted by the user. As shown in FIG. 3, the user 150 uses a web browser 152 to access the Internet 154. The user 150 is able to create images 180 of their face 182, such as that shown in FIG. 4, using a digital camera or a scanner 156. The digital image 180 can then be transmitted over the Internet 154 via the web browser 152.

The web server 160 that contains the crucial elements of the present invention is accessible to the web browser 152 through the Internet 154. The web server 160 ideally contains e-commerce software 162 that allows the user 150 to view, select, order, and pay for eyewear through the web browser 152. Such e-commerce software 162 is well known in the prior art.

The web server 160 of the present invention is capable of receiving images 180 through image reception component 164. The capability of receiving images 180 at a web server and associating the image 180 with a particular user 150 is easily implemented. Some techniques that are currently used include the storage of the image 180 at the server 160 and using cookies to identify and associate the image 180 with a particular user 150. Other techniques include the use of login IDs and passwords.

The submitted image 180 can then be used by "virtual try-on" software 166, which is also known in the prior art. This software 166 is capable of superimposing on the received facial image 180 a representation of eyeglasses frames 184 selected by the user 150, as is shown in image 181 of FIG. 5. This new image 181 is accomplished by resizing the original image 180 so that the eyes 186 on the face 182 are at a known distance apart. The image 181 is then repositioned so that the exact location of the eyes 186 is the same on each image 180 received. The eyes 186 in the image 180 can be located either by having the user locate the eyes 186 (such as by a request to "click" on each eye) or by using image recognition software to locate the eyes 186.

Figure 5:
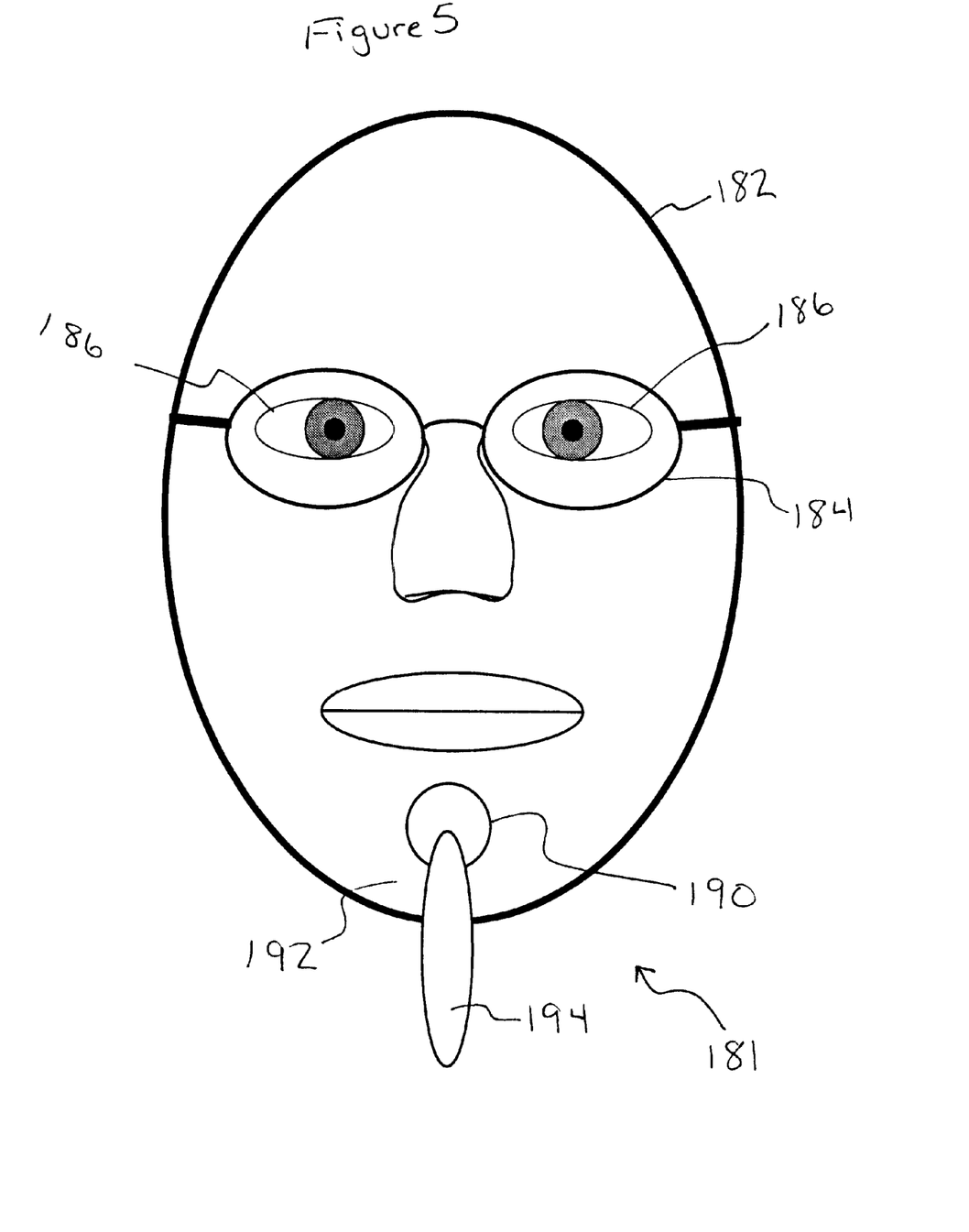
FIG. 5 is an illustration of the use a superimposed frame image on the face in conjunction with the system and method of FIG. 3.

Once the image 181 is resized and repositioned, the software 166 knows the exact location of the eyes 186 in the image 181. At this point, the representation of the eyeglasses frames 184 can be superimposed at the same place on every image 181. Since the image 181 has been resized so that the eyes 186 are a known distance apart, a relatively good try-on image 181 can be created without even scaling the frames 184. This is accomplished simply by pre-scaling the frames so that the preferred eye location in the frames is the same as the known eye distance. Unfortunately, creating a virtual try-on image 181 in this manner does not show the relative size difference between frames 184, since both large and small frames 184 will be scaled to look similar on image 181. If the image 181 is first scaled according to the technique of the present invention set forth below, this disadvantage can be avoided and a more useful try-on image 181 is created.

Figure 4:
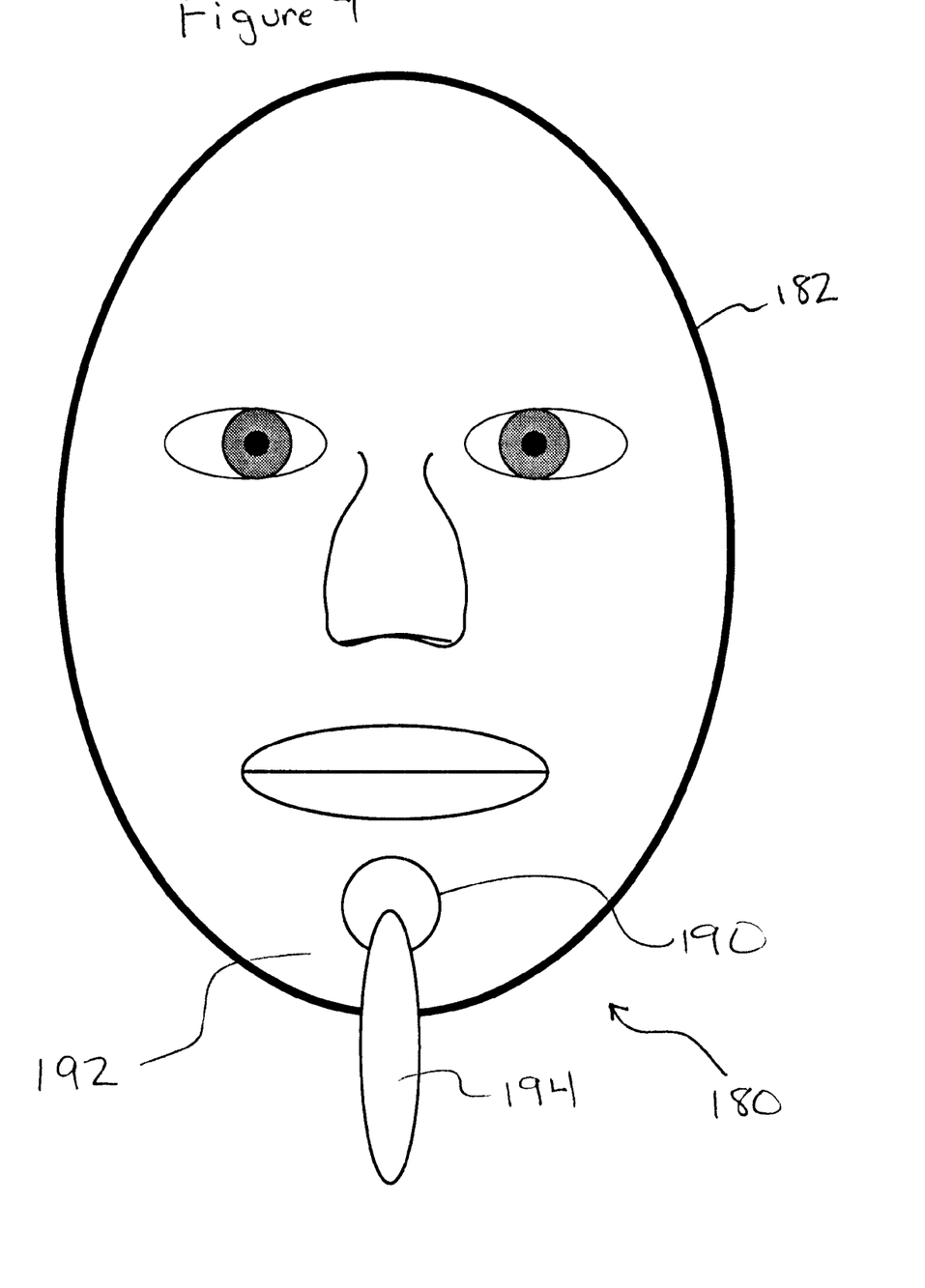
FIG. 4 is an illustration of the positioning of a reference object in conjunction with the system and method illustrated in FIG. 3.

In a first embodiment of the present invention, the user 150 submits a facial image 180 with a reference object 190 in it, such as shown in FIG. 4. The user 150 is instructed how to do this through the web pages presented by the server 160 to the browser 152. The reference object 190 must be of a size known to the server 160, and must be readily available to the user 150. Ideally, the reference object 190 is circular in shape.

The reference object 190 must have the same relative size in the image 180 as the face 182 of the user 150. Thus, the object 190 must be the same distance from the camera as the face 182. In addition, if the reference object 190 is flat or relatively 2-dimensional, the object should be on the same general plane as the face 182, with such plane generally perpendicular to the camera. To accomplish these objectives, the user 150 may be requested to hold the object on their chin 192 with their finger 194. The user 150 should be instructed not to completely obscure the reference object 190 in the image 180.

The scale image module 168 of server 160 is used to determine the scale of the received image 180. In a first embodiment, a technician 170 uses this module 168 by connecting with the server 160 either locally or through the Internet 154. The component 168 is used to determine the width in pixels of the reference object 190 in image 180. Once determined, this pixel distance is used in combination with the known real-world width of the reference object 190 to create a scale of image 180, as described below in connection with FIG. 6.

The pupillary distance determination module 172 is also accessible to technician 170. The technician 170 uses this module 172 to determine the pupillary distance 100 in pixels on image 180. Once this is determined, the scale determined in module 168 is used to calculate the actual PD 100 of user 150.

The seg height determination module 174 functions similarly. The technician 170 uses the module 174 to find the seg height 108 in pixels, using the composite image 181. The scale is then applied to calculate an actual seg height 108 for user 150.

Figure 6:
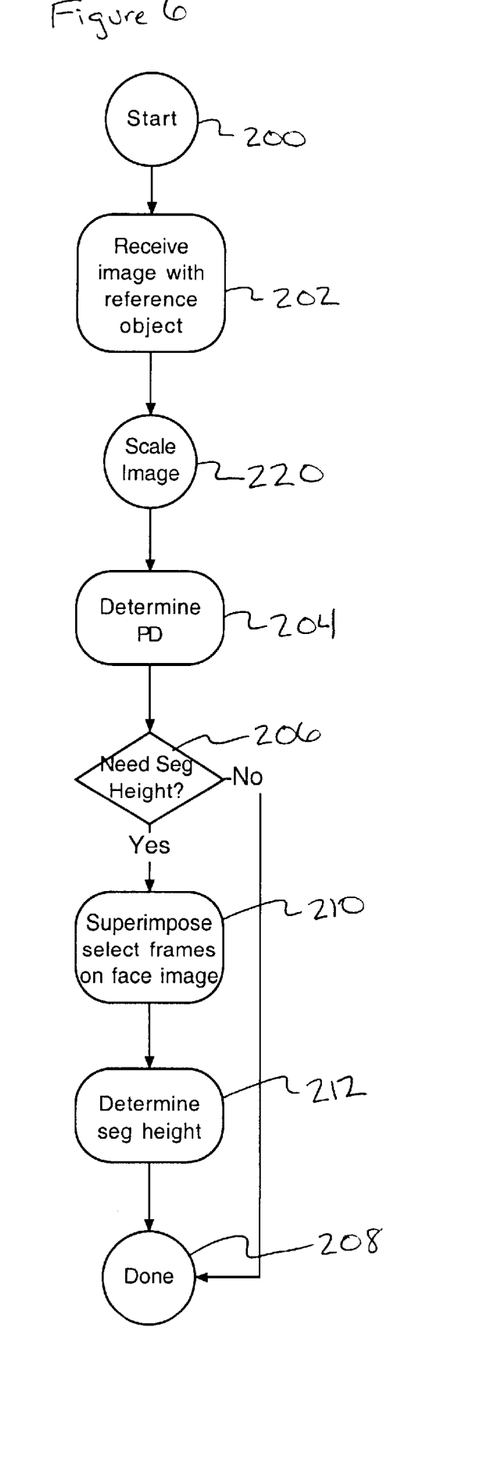
FIG. 6 is a flow chart illustrating the steps for calculating significant parameters in conjunction with the system and method of FIG. 3.

The method 200 used by the present invention to calculate the PD 100 and seg height 108 for the user 150 is shown in FIG. 6. The first step 202 is to receive a facial image 180 of the user 150. In the first embodiment of the present invention, a reference object 190 is required to be in the photograph in order to properly scale the image.

Figure 7:
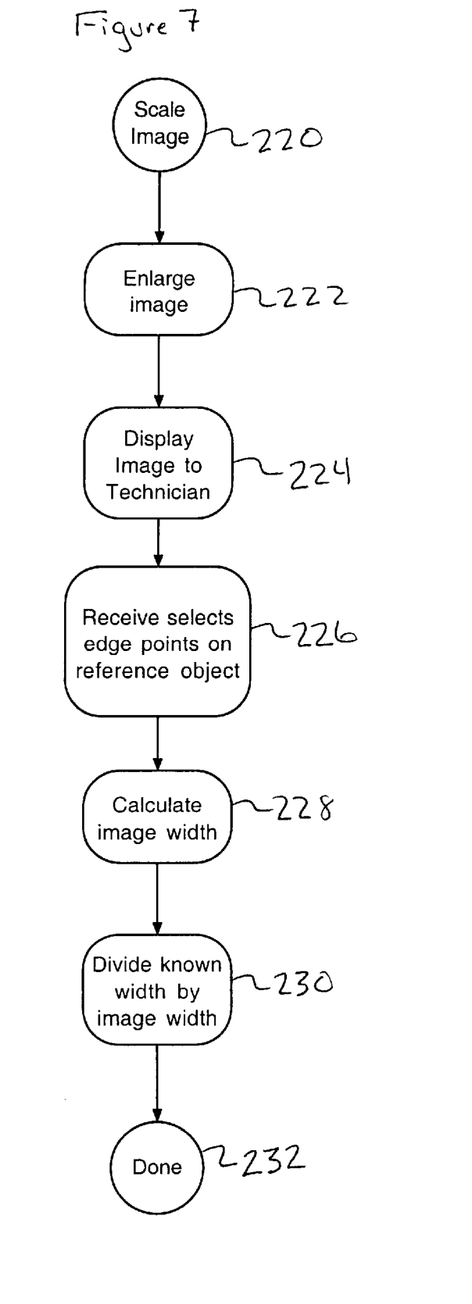
FIG. 7 is a flow chart illustrating steps for scaling an image in conjunction with the system and method of FIG. 3.

The next step in method 200 is to scale the image through process 220, which is shown in FIG. 7. The first step in of process 220 is to enlarge the image 180 (step 222). It is possible to skip this step. However, in most cases it is easier for the technician to make accurate selections in later steps if the image 180 is enlarged. When enlarging a pixelated digital image, it is possible simply to fill multiple pixels with the value of a single pixel in the original image (known as pixel resize). Alternatively, and preferably, techniques can be used that intelligently enlarge a pixelated image by interpolating how new pixels should appear, then filling them in with the appropriate color. One known technique for performing such interpolation is the bi-cubic technique. Other techniques for enlarging an image, whether now known or hereinafter developed, could be used in step 222.

Once this image 180 is enlarged, it is displayed to the technician 170 in step 224. In step 226, the technician selects two edge points on the reference object 190, such as by clicking on opposite sides of the enlarged image of the object 190. The distances from the two selected edge points on the reference object 190 must be known to the present invention. Consequently, it is preferred to have the reference object 190 be a circular object of a known diameter, so that the edge points can simply be any two points found on opposite sides of the circular reference object 190. Other shapes are certainly possible, but in those cases the user 150 must be sure not to obscure one of the endpoints needed to select the known distance.

In step 228, it is necessary to determine the length between the two edge points in the image. While this can be done with a ruler, it is easier to measure the distance between the two points in a digital image in pixels. This is done using the Pythagorean theorem: for a right triangle, the square of the hypotenuse is equal to the sum of the squares of the other two sides. Thus, for two points in a pixelated digital image, with each point having an x and y coordinate, the number of pixels between the selected points is:

$$\sqrt{(x1-x2)^2+(y1-y2)^2}$$

or the square root of the difference of the x coordinates squared plus the difference of the y coordinates squared.

To determine the appropriate scale in step 230, it is now only necessary to divide the known real-world width of the reference object by the image width calculated in step 228. For instance, if the reference object were a coin having a diameter of 25 mm, and the image of the reference object had a diameter of 50 pixels, then the scale would be 0.5 mm per pixel. The process 200 of scaling the image 180 is then complete at step 232.

Figure 8:
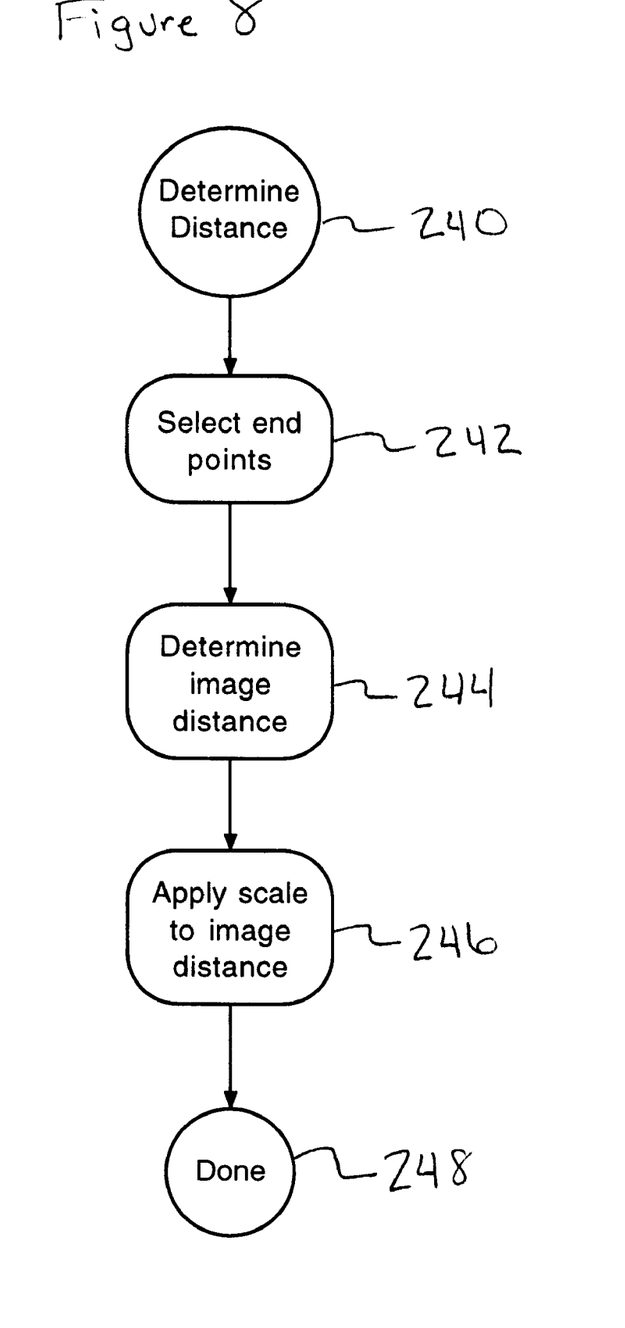
FIG. 8 is a flow chart illustrating steps for determining any distance in a scaled image in conjunction with the system and method of FIG. 3.

Returning to FIG. 6, once the scale is determined in process 220, it is necessary to determine the pupillary distance 100 in step 204. This can be accomplished by applying the scale determined in step 220 to the distance between the pupils 102 in image 180. The method of doing so is the same as the method for determining any distance in a scaled image 180, which is set forth in FIG. 8 as process 240. First, the end points of the distance are selected in step 242. This can be done by the technician 170 through the same interface used to determine the image width of the reference object 190 in process 220. For instance, to determine the PD 100, the technician 170 would merely click once in the center of each pupil 102 in the image 180 (or on the left side of each iris 106). Once the end points are selected, the image distance is determined in step 244, such as by using the Pythagorean theorem as done in step 228. In step 246, the scale calculated in process 220 is applied by multiplying the image distance of step 244 by the scale, and the process is complete at step 248.

Returning to FIG. 6, the next step 206 after determined the pupillary distance 100 is to determine whether the seg height 108 needs to be determined. As explained above, the seg height 108 is needed only when user 150 orders multi-focal lenses. If multi-focal lenses are not ordered, no seg height 108 is needed and step 206 determines that process 200 is complete at step 208.

To determine the seg height 108, it is necessary to know where the bottom 112 of the frame 114 is located relative to the eye 104, as shown in FIG. 2. This is accomplished in the present invention by superimposing an image of the selected frame 184 over the face 182 in step 210, as was described above in connection with FIG. 5. Assuming the scale of process 220 was accomplished using this same image 181, it is a simply matter to determine the seg height in step 212. The technician 170 is presented the superimposed image 181, and asked to select the points corresponding to bottom of the superimposed frame 184 and the desired location of the seg height 108 (i.e., lower lid, just above the lower lid, or pupil height). In fact, it would be possible to only require the technician to indicate the latter position, since it would be a simple matter to determine the bottom point of the superimposed frame 184 electronically in the try on technology software. The distance from the bottom of the frame 184 and the desired seg height is then calculated as explained above through process 240. Once the seg height 108 is calculated, the process 200 of determining the PD 100 and seg height 108 terminates at step 208.

In this way, process 200 allows the determination of the PD 100 of user 150 through a submitted photograph without any direct examination of the user 150. If needed, process 200 will also determine the seg height 108. Since this determination relies on the proper scaling and measurement of distances on a submitted digital image, it is to be expected that this method 200 is not as accurate as direct examination of the user 150. However, tests have found that the PD 100 determined by this method 200 are within the margin of error needed for the accurate grinding of prescription lenses.

A second embodiment of the present invention replaces the technician 170 by having user 150 identify the edges of the reference object, the pupils, the seg height position, and the lower edge of the frames (if necessary). Although this makes the process somewhat more complicated for the user, overhead would be lowered because there would be no need for the steps to be done by a paid technician.

A third embodiment of the present invention replaces the technician 170 with image recognition software. Image recognition technology has improved greatly over the last five years, and will continue to improve. The image recognition tasks of the present invention are straightforward and easily implemented. The tasks of the technician that would need to be replaced are as follows:

Recognition of the reference object 190 and determine the two points that reflect the known distance;

Recognition and location of the pupils 102 and/or iris 106 of the user 150 for calculating the pupillary distance 100;

Recognition and location of the lower eye lid of the user 150 for determination of the seg height 108

Each of these tasks can be accomplished with current image recognition technology, and should become easier as the technology advances in the coming years. The try-on software component 166 can also use image recognition technology so that the user 150 does not need to locate their eyes in the submitted image 108.

In a fourth embodiment of the present invention, a reference object 190 does not need to be included in the submitted image 180. Instead of the reference object 190 of a known width, the image is scaled in process 220 by using one of the irises 106 in the eye 104 of the facial image 180. It is well known that the iris 106 of an adult human is of a relatively fixed size from individual to individual. Specifically, as shown in FIG. 1, the iris 106 has a diameter 107 that is approximately 12 mm. The use of the iris 106 as the reference object is less precise, since the size of the iris 106 has some variability, but it has the advantage of not requiring the user 150 to include an additional object in the submitted facial image 180.

The invention is not to be taken as limited to all of the details thereof as modifications and variations thereof may be made without departing from the spirit or scope of the invention. For instance, the present invention shows multiple modules residing on the web server of the present invention. It would be easy to move some of the modules off the server onto one or more additional computers. This could help limit the load on the server. Alternatively, moving certain modules could be done simply to move some of the PD and seg height determination elements to the actual lab where the lens is to be ground and a technician may be found.

In addition, while the described embodiments of the present invention utilized circular reference objects 190, other shapes are certainly possible. Also, while one of the described embodiments utilized the size of the human iris 106 as the reference object 190, any other human features that may be found to have a relatively consistent size may be used. Many possible combinations of features and elements are possible within the scope of the present invention, and therefore the scope thereof should be limited only by the following claims.

What is claimed is:

1. A method for determining the real-world pupillary distance of a patient from a photograph comprising:

a) receiving a photograph containing a face of the patient, the photograph showing a reference object of a known real-world size;

b) determining a scale of the photograph by comparing the known realworld size of the reference object with the size of the reference object in the photograph;

c) determining the photograph pupillary distance of the face on the photograph; and d) applying the scale to the determined photograph pupillary distance to calculate the real-world pupillary distance.

2. The method of claim 1, wherein the reference object is circular.

3. The method of claim 2, wherein the reference object is a monetary coin.

4. The method of claim 1, wherein the reference object is an iris of the patient.

5. The method of claim 1, wherein the reference object is on approximately the same plane as the face.

6. The method of claim 1, wherein the step of determining the scale is accomplished by:

i) measuring the distance on the photograph between two points on the reference objects; and ii) dividing the measured distance by the known real-world distance between those two points.

7. The method of claim 6, wherein the photograph is received in digital format, and the step of measuring the distance on the photograph between two points on the reference object is accomplished by:

(1) selecting a first point on the reference object;

(2) noting the x and y pixel coordinates of the first point;

(3) selecting a second point on the reference object;

(4) noting the x and y pixel coordinates of the second point;

(5) determining the pixel distance between the first and second points using the Pythagorean theorem.

8. The method of claim 7, wherein the step of determining the photograph pupillary distance is accomplished by:

i) selecting a location on a first eye in the photograph;
ii) noting the x and y pixel coordinates of the first eye location;
iii) selecting a location on a second eye in the photograph;
iv) noting the x and y pixel coordinates of the second eye location;
v) determining the pixel distance between the first eye location and the second eye location using the Pythagorean theorem.

9. The method of claim 8, wherein the locations on the first and second eye are selected by presenting the image to a technician who moves a pointer over the image to select the locations.

10. The method of claim 8, wherein the locations on the first and second eye are selected via automated image recognition routines without manual location selection by a technician.

11. The method of claim 8, wherein the locations on the first and second eye are preliminarily selected via automate image recognition routines and then verified by a technician.

12. The method of claim 1, further comprising the following step:
e) after receiving the photograph, enlarging the photograph to make steps b) and c) easier.

13. The method of claim 12, wherein the step of enlarging the photograph is accomplished through interpolating the new pixels based on the value of current pixels.

14. The method of claim 13, wherein the interpolating is done through the bi-cubic technique.

15. The method of claim 1, further comprising the following step:
f) superimposing an image of an eye glasses frame over a received facial photograph to create an new image showing the frame as if it were being worn in the facial photograph.

16. The method of claim 15, further comprising the following step:
g) determining where multi-focal elements should be placed in the eye glasses frame by
i) selecting a first point on the new image at the bottom of the frame;
ii) selecting a second point on the new image at an appropriate place on the eye;
iii) determining the distance between the first and second point on the new image;
iv) applying the scale to the distance between the first and second point.

17. A web site for receiving orders for an eye glasses frame over the Internet, the web site comprising:
a) an image submission portion capable of receiving a digital image of a face and a reference object of a known real-world size from an end user;
b) a scale image portion where the scale of the digital image is determined by comparing the size of the reference object in the image with the known real-world size of the reference object; and
c) a pupillary distance determination portion that determines the real world pupillary distance of the face by comparing the image pupillary distance with the determined scale of the digital image.

18. The web site of claim 17, wherein the reference object is circular.

19. The web site of claim 17, wherein the reference object is an iris of an eye found on the face.

20. The web site of claim 17, further comprising:
d) an image enlargement portion that enlarges the received digital image to aid the scale image portion and the pupillary distance portion.

21. The web site of claim 20 wherein the image enlargement portion uses an interpolation technique to determine the value of new pixels.

22. The web site of claim 17, wherein the reference object selection portion has:
i) a reference object point selection portion that selects two reference object points on the image of the reference object that have a known real-world distance;
ii) a calculating portion that determines the pixel distance between the two reference object points and determines the scale of the image by comparing the pixel distance with the known real-world distance.

23. The web site of claim 21, wherein the reference object point selection portion further comprises:
(1) an image presentation portion that presents the image to an individual;
(2) a point selection means for allowing the technician to manually select points on the image.

24. The web site of claim 23, wherein the individual is a technician other than the patient.

25. The web site of claim 23, wherein the individual is the same as the patient.

26. The web site of claim 21, wherein the reference object point selection portion further comprises image recognition routines that can select the reference object points without manual selection of points by a technician.

27. The web site of claim 17, further comprising:
d) an superimposing portion that superimposes the image of a selected eyeglasses frame over the digital image of the face creating a superimposed image; and
e) a multi-focal height selection portion that determines the appropriate location of multi-focal elements in the selected eyeglasses frame utilizing the superimposed image of the frame over the digital image of the face in combination with the scale of the digital image.

28. The web site of claim 27, further comprising:
f) an image presentation portion for presenting the superimposed image of frame and face to the end user to aid in the selection of eyeglasses frames.

29. The web site of claim 27, wherein the multi-focal height selection portion further comprises:
i) an image presentation portion that present the superimposed image to an individual;
ii) a point selection means for allowing the individual to manually select points on the superimposed image relating to the bottom of the frame and the appropriate height on the eye for the multi-focal element.

30. The web site of claim 27, wherein the multi-focal height selection portion further comprises image recognition routines that can select the bottom portion of the frame and the appropriate height on the eye without manual selection of points by a technician.

31. A system for determining the pupillary distance of a patient from a photograph comprising:
a) means for receiving a photograph showing a face of the patient and a reference object of a known real-world size on approximately the same plane as the face;
b) means for determining a scale of the photograph by comparing the known real-world size of the reference object with the size of the reference object in the photograph;
c) means for determining the photograph pupillary distance of the face on the photograph; and
d) means for multiplying the determined photograph pupillary distance by the scale.

* * * * *